United States Patent [19]

Harada

[11] 4,311,144
[45] Jan. 19, 1982

[54] ELECTRICAL SURGICAL KNIFE DEVICE

[75] Inventor: Shinichi Harada, Tsurugashima, Japan

[73] Assignee: Kabushiki Kaisha Medos Kenkyusho, Tokyo, Japan

[21] Appl. No.: 136,611

[22] Filed: Apr. 2, 1980

[30] Foreign Application Priority Data

Apr. 13, 1979 [JP] Japan .............................. 54-49067[U]

[51] Int. Cl.³ .............................................. A61B 17/39
[52] U.S. Cl. ................................ 128/303.15; 128/908
[58] Field of Search ...................... 128/303.13, 303.14, 128/303.15, 303.16, 303.17, 303.18, 908

[56] References Cited

U.S. PATENT DOCUMENTS

| | | | |
|---|---|---|---|
| 3,804,096 | 4/1974 | Gonser | 128/303.14 |
| 3,999,552 | 12/1976 | Huggins | 128/303.13 |
| 4,054,143 | 10/1977 | Bauer | 128/303.17 |
| 4,121,590 | 10/1978 | Gonser | 128/303.13 |
| 4,184,492 | 1/1980 | Meinke et al. | 128/303.14 |

*Primary Examiner*—Lee S. Cohen
*Attorney, Agent, or Firm*—Sughrue, Mion, Zinn, Macpeak & Seas

[57] ABSTRACT

An electrical surgical knife which may be inserted into a body cavity of a patient through an endoscope in which electrical shock to the patient or user of the knife is prevented. A positive polarity electrode of the knife is disposed inside a flexible insulating tube. Around all but an end protruding active portion of the positive polarity electrode there is disposed a conductive metal sheath which is insulated therefrom. The metal sheath is electrically connected to a metal plate electrode which is adapted to be disposed in electrical contact with the skin of a patient.

2 Claims, 3 Drawing Figures

ELECTRICAL SURGICAL KNIFE DEVICE

BACKGROUND OF THE INVENTION

The present invention relates to an electrical surgical knife which may be inserted into a body cavity of a patient, for instance, to cut an affected part. More particularly, the invention relates to an improved electrical surgical knife device a specific feature of which resides in its electrical insulating means.

As is well known in the art, an electrical surgical knife is operated as follows. High frequency electric power is applied across the plate side of the knife which is brought into contact with the skin of a patient and the positive polarlity side of the knife the edge of which is brought into contact with the affected part. As the high frequency current flows collectively through the edge of the positive polarity side, Joule heating is generated at the edge. This heat is utilized to burn or cut the affected part.

A device including both an electrical surgical knife and an endoscope for treating an affected part of the body cavity which the operator cannot see directly has been put in practical use. In a conventional such device, the positive polarity side circuit of the surgical knife, which is relatively long, upon being inserted into the body cavity extends along the wall of the body cavity. Therefore, the circuit must be electrically well insulated. For this purpose, the positive polarity side circuit line is covered with a silicon tube. However, high frequency current sometimes leaks through pin holes in the covering tube which may damage a part of the wall of the body cavity.

In order to prevent the occurrence of such problems due to current leakage, means for forming a short-circuit of leakage current have been proposed in which the metal blade of the flexible pipe of an endoscope into which the positive polarity side is inserted and the endoscope body, which is integral with the metal blade, are electrically connected to the aforementioned plate side which is brought into contact with the skin of a patient.

However, it should be noted that, with the conventional construction, high frequency leakage currents flow in the endoscope body and, if the patient or the operator touches the endoscope body carelessly, he may be shocked or burnt by current which flows through his body to ground.

Accordingly, an object of the invention is to provide an electrical surgical knife device in which the above-described problems due to the leakage current problems accompanying a conventional device of this type are prevented.

SUMMARY OF THE INVENTION

In accordance with this and other objects of the invention, there is provided an electrical surgical knife adapted to be inserted into a body cavity of a patient through an endoscope including a flexible insulating tube through which is disposed a positive polarity electrode of the surgical knife. A metal sheath is disposed inside the tube around portions of the positive polarity electrode but insulated from the positive polarity electrode. The positive polarity electrode is adapted to be connected to a source of high frequency electricity. A metal plate electrode, which is adapted to be disposed in contact with the skin of a patient is electrically connected to the metal sheath to thereby prevent leakage of high frequency electric current and to thereby prevent electrical shock to the patient or operator of the device.

DESCRIPTION OF THE PREFERRED EMBODIMENTS

Figure 1:
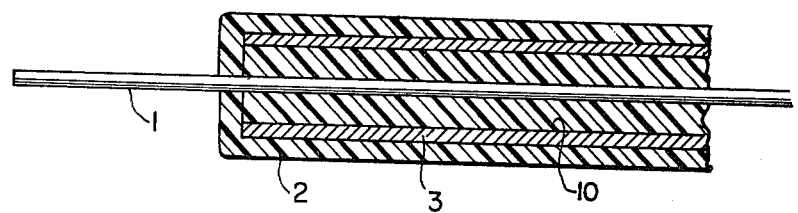
FIG. 1 is a longitudinal sectional view showing the essential components of a preferred embodiment of an electrical surgical knife device according to the invention.
Figure 2:
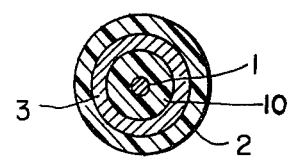
FIG. 2 is a cross sectional view taken through FIG. 1.

FIG. 1 is a fragmented sectional view showing the essential components of a preferred embodiment of an electrical surgical knife device according to the invention while FIG. 2 is a cross-sectional view thereof. The surgical knife of the invention includes an insulating tube 2 which is hollow and flexible and a positive polarity side circuit line 1 disposed inside the insulating tube 2. A flexible cylindrically shaped metal sheath 3 is disposed in the wall of the insulating tube 2. An insulating tube 10 isolates the positive polarity circuit line 1 from the metal sheath 3.

Figure 3:
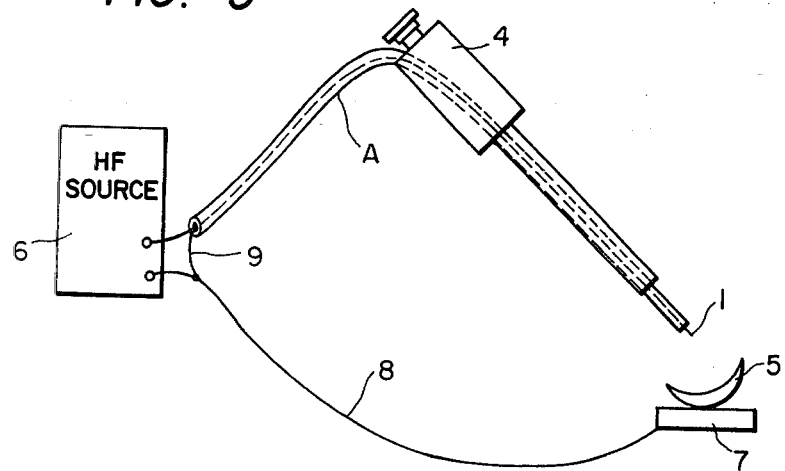
FIG. 3 is an explanatory diagram showing an arrangement of the device according to the invention.

FIG. 3 is an explanatory diagram showing the arrangement of the preferred embodiment of the electrical surgical knife device accordng to the invention. A positive polarity side structure A of the surgical knife constructed as described above is inserted into an endoscope 4 before the surgical knife is inserted into the body cavity. The positive polarity side circuit line 1 is connected to one electrode of a high frequency electric source 6 while the other electrode is coupled through a metal plate 7 to a circuit line 8. The metal plate 7 is maintained in contact with the skin of the patient 5. Furthermore, the metal sheath 3 of the structure A is connected through a conductor 9 to the metal plate 7.

In carrying out medical treatment with the device of the invention thus constructed, first the electrical surgical knife and the endoscope 4 are assembled as shown in FIG. 3. Then, while the body cavity is being observed with an observing device, an edge provided at the end of the positive polarity side circuit line 1 is brought into contact with the affected part of the body cavity such as the stomach. Under this condition, the high frequency electric source 6 is switched on and high frequency current flows between the circuit line 1 and the metal plate 7 brought into contact with the patient's body through his skin. As the high frequency current flows collectively through the edge of the circuit line 1, heat is generated at the edge which is used to burn or cut the affected part of the body cavity.

The positive polarity side circuit line 1 is electrically insulated by the insulating tube 2 with leakage current through the insulating tube 2 made to flow through the metal sheath 3 to the metal plate. Therefore, while high frequency current is supplied to the circuit line 1, no problem caused by leakage current results.

In the device according to the invention, the metal sheath 3 is entirely covered by the insulating tube 2 so that the endoscope 4 is electrically insulated not only from the positive polarity side but also from the metal plate. Therefore, even if the patient or the operator touches the endoscope, he will never be shocked. Thus, the device of the invention is quite safe.

In the above-described example of the device according to the invention, the metal sheath 3 is disposed within the insulating tube 2 which covers the positive polarity side circuit line 1. However, in the case where a forceps channel of the endoscope 4 is employed as the positive polarity side insertion path, the conventional positive side structure, the surface of which is coated with Teflon (TM) or the like, can be used after it is inserted into the forceps channel if the tube of the forceps channel is employed as the insulating tube in which the metal sheath is disposed.

As is clear from the above description, in the device of the invention, the endoscope body is electrically insulated from the positive polarity side of the electrical surgical knife and the metal plate. Therefore, electrical shocks or burns due to leakage current flowing from the endoscope body through a human body to ground are prevented.

What is claimed is:

1. An electrical surgical knife adapted to be inserted into a body cavity of a patient through an endoscope comprising: a flexible insulating tube; a positive polarity electrode of said surgical knife disposed in said tube; a coaxial layer of insulating material disposed around said positive electrode; a metal sheath disposed inside said tube around portions of said positive polarity electrode disposed within said tube and insulated from said positive polarity electrode by said coaxial layer of insulating material, said positive polarity electrode being adapted to be connected to a high frequency electrical source; and a metal plate electrode adapted to be disposed in contact with the skin of a patient, said metal sheath electrically connected to said metal plate.

2. An electrical surgical knife adapted to be inserted into the body cavity of a patient through an endoscope comprising: a center positive polarity electrode; a coaxial cylindrical first layer of insulating material disposed around portions of said positive polarity electrode with an end portion of said positive polarity electrode protruding outwardly from an end thereof; a conductive metal sheath disposed around said first layer of insulating material; a second layer of insulating material disposed around said conductive metal sheath and covering end portions of said first layer of insulating material and said metal sheath at the end from which said positive polarity electrode protrudes; and a conductive metal plate electrode adapted to be disposed in contact with the skin of a patient, said metal plate electrode being electrically connected to said conductive metal sheath.

* * * * *